(12) United States Patent
Herrmann et al.

(10) Patent No.: US 12,181,618 B2
(45) Date of Patent: Dec. 31, 2024

(54) RADIOLOGICAL INSTRUMENT WITH A PULSE SHAPER CIRCUIT

(71) Applicant: KONINKLIJKE PHILIPS N.V., Eindhoven (NL)

(72) Inventors: Christoph Herrmann, Aachen (DE); Yoad Yagil, Haifa (IL); Roger Steadman Booker, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 364 days.

(21) Appl. No.: 17/786,193

(22) PCT Filed: Dec. 23, 2020

(86) PCT No.: PCT/EP2020/087818
§ 371 (c)(1),
(2) Date: Jun. 16, 2022

(87) PCT Pub. No.: WO2021/130338
PCT Pub. Date: Jul. 1, 2021

(65) Prior Publication Data
US 2023/0029181 A1    Jan. 26, 2023

(30) Foreign Application Priority Data
Dec. 23, 2019  (EP) ..................... 19219191

(51) Int. Cl.
*A61B 6/42*     (2024.01)
*A61B 6/03*     (2006.01)
*G01T 1/24*     (2006.01)
(52) U.S. Cl.
CPC .................. *G01T 1/24* (2013.01); *A61B 6/03* (2013.01); *A61B 6/4208* (2013.01)

(58) Field of Classification Search
CPC ............ G01T 1/24; A61B 6/03; A61B 6/4208
(Continued)

(56) References Cited

U.S. PATENT DOCUMENTS 10,996,351 B2    5/2021   Steadman Booker
2008/0018505 A1   1/2008   Astley
(Continued)

FOREIGN PATENT DOCUMENTS

EP           3385756 A1    10/2018

OTHER PUBLICATIONS

PCT International Search Report, International application No. PCT/EP2020/087818, Mar. 18, 2021.
(Continued)

*Primary Examiner* — David P Porta
*Assistant Examiner* — Carolyn Fin
(74) *Attorney, Agent, or Firm* — Larry Liberchuk (57) ABSTRACT

Disclosed herein is a radiological instrument (100, 200, 300, 400, 600, 700, 800) comprising at least one pulse shaper circuit (102) configured for a direct conversion radiation detector (108). The at least one pulse shaper circuit comprises an amplifier (110). The pulse shaper further comprises a feedback circuit (118) connected in parallel with the amplifier; a first switching unit (120) connected in series with the feedback circuit; a second switching unit (122) connected in parallel with the amplifier; a discriminator circuit (124) that provides a discriminator signal (128) when the output exceeds a controllable signal threshold; and a control unit (124) for controlling the first switching unit and the second switching unit, wherein the control unit controls the second switching unit such that a substantial part of the signal is integrated, when the second switching unit is closed.

10 Claims, 8 Drawing Sheets

(58) Field of Classification Search
USPC .................................................. 250/370.09
See application file for complete search history.

(56) References Cited

U.S. PATENT DOCUMENTS

| | | | |
|---|---|---|---|
| 2010/0172467 A1 | 7/2010 | Steadman Booker | |
| 2010/0187432 A1 | 7/2010 | Herrmann | |
| 2010/0329425 A1* | 12/2010 | Guo | G01T 1/247 378/91 |
| 2011/0036989 A1* | 2/2011 | Marks | G01T 1/17 250/370.08 |
| 2013/0284940 A1 | 10/2013 | Herrmann | |
| 2015/0061735 A1* | 3/2015 | Lee | G01T 1/24 327/143 |
| 2015/0309188 A1 | 10/2015 | Roessl | |
| 2016/0070005 A1 | 3/2016 | Sagoh | |
| 2016/0299002 A1 | 10/2016 | Steadman Booker | |
| 2020/0064500 A1* | 2/2020 | Steadman Booker | H03K 5/1532 |

OTHER PUBLICATIONS

Krummenacher F. et al., "Pixel Detectors with Local Intelligence—An IC Designer Point of View", Nuclear Instruments & Methods in Physics Research, Section A, Accelerators, Spectrometers, Detectors and Associated Equipment, vol. 305, Issue 3, pp. 527-532, 1991.

Kraft E. et al., "Counting and Integrating Readout for Direct Conversion X-Ray Imaging: Concept, Realization and First Prototype Measurements", IEEE Transactions on Nuclear Science, vol. 54, No. 2, pp. 383-390, Apr. 2007.

Knoll G. et al., "Radiation Detection and Measurement", J. Wiley, Third Edition, 2010, Chapter 4 pp. 119-128, Chapter 17, p. 626.

* cited by examiner

RADIOLOGICAL INSTRUMENT WITH A PULSE SHAPER CIRCUIT

TECHNICAL FIELD

The invention relates to the detection of ionizing radiation, in particular to systems that use direct-conversion x-ray detectors.

BACKGROUND OF THE INVENTION

Current pulses for direct conversion radiation detectors, such as CZT, are converted into voltage pulses using shaper circuits. When detecting X-rays with direct conversion radiation detectors, the ballistic deficit (BD) effect can cause output pulses from the shaper circuit for X-rays that have the same energy to have slightly different amplitudes. These slight variations in the amplitude caused by the BD can increase noise or affect image quality in general in computed tomography (CT) system.

United States patent application publication US 20160299002 A1 discloses a detection device for detecting photons emitted by a radiation source and capable of adjusting ballistic deficit. The detection device comprises a pre-amplifying unit (such as, e.g., a charge-sensitive amplifier), a shaping unit comprising a feedback discharge unit, and a feedback discharge control unit coupled to the feedback discharge unit. The feedback discharge control unit is adapted to, e.g., adjust a resistance of a feedback resistance (and/or to adjust the current value of the feedback current source) if an electrical pulse generated by the shaping unit does not exceed at least one energy comparison value. The feedback discharge control unit is adapted to not adjust the parameter of the feedback discharge unit if the electrical pulse exceeds the at least one energy comparison value. By tuning the feedback resistance operating point, the ballistic deficit can be adjusted to a predefined expected value.

SUMMARY OF THE INVENTION

The invention provides for a radiological instrument, an imaging system, a computer program product, and a method in the independent claims. Embodiments are given in the dependent claims.

Embodiments may provide for an improved method of reducing or eliminating the ballistic deficit effect in a pulse shaper circuit. Embodiments may do this by providing for a pulse shaper circuit that includes an amplifier configured as an integrator. There may be a feedback capacitance between the input and the output of the amplifier. In addition, there is a feedback circuit connected in parallel with the feedback capacitance or with the input and output of the amplifier. The feedback circuit may be a current source in some examples or a discharge resistance. The discharge resistance may also be referred to as a feedback resistance. A first switching unit may be in parallel with the input and output of the amplifier. When the first switching unit is open, the feedback circuit is effectively removed from the circuit.

A second switching unit may be connected to the input and output of the amplifier, when the second switching unit is closed the second switching unit functions as a short circuit to rapidly reset the integrator or equivalently discharge the feedback capacitance if it is present. The second switching unit may be in series with a short circuit resistance. If present, the short circuit resistance may be chosen so that it more rapidly drains the feedback capacitance than the feedback circuit would do.

In some examples a control unit for controlling the first switching unit and the second switching unit may be provided. In this example, the control unit controls the second switching unit such that a substantial part of the signal is integrated, when the second switching unit is closed.

A discriminator circuit may be connected to the output of the amplifier. If the voltage output rises above a controllable signal threshold then the discriminator circuit sends a discriminator signal in some examples to a timing circuit. The timing circuit may then immediately open the first switching unit and remove the feedback circuit from the circuit. After a first delay, the timing circuit then closes the second switching unit to discharge the feedback capacitance. The first delay is long enough so that the signal from the direct conversion radiation detector is collected. After the second switching circuit is closed, the timing circuit waits a second delay until the timing unit opens the second switching circuit. The second delay may be chosen so that the feedback capacitance is discharged or sufficiently discharged. In some examples, while the second switching unit is closed, the timing circuit closes the first switching circuit.

The first switching unit thus opens to remove the effect of the discharge resistance on the circuit when the output signal is above the controllable signal threshold and the second switching unit, after the first delay, returns the feedback capacitance to a consistent state for the next pulse shaping event. The effect of using these two switching units is that the BD may greatly be reduced. In comparison to other solutions for reducing the BD the circuit is simplified. When used in the imaging systems, such as medical systems, such as CT systems, there may be a reduction in image artifacts due to the reduced BD.

In one aspect the invention provides for a radiological instrument that comprises at least one pulse shaper circuit. The at least one pulse shaper circuit is configured for receiving an input signal from a direct conversion radiation detector. In direct conversion radiation detectors, an ionizing radiation enters the direct conversion radiation detector and creates a current directly. Typically, direct conversion radiation detectors are semiconductors.

The at least one pulse shaper circuit comprises a shaper input configured for receiving the input signal. Each of the at least one pulse shaper circuit comprises a shaper input. The at least one pulse shaper circuit further comprises a shaper output configured for providing an output signal in response to the input signal. Each of the at least one pulse shaper circuits comprise a shaper output. The at least one pulse shaper circuit further comprises an amplifier with an amplifier input connected to the shaper input and an amplifier output connected to the shaper output. The amplifier is configured as an integrator. There is an amplifier for each of the at least one pulse shaper circuit.

The at least one pulse shaper circuit may further comprise a feedback capacitance connected between the amplifier input and the amplifier output. Each of the at least one pulse shaper circuit may comprise a distinct or separate feedback capacitance. The at least one pulse shaper circuit further comprises a feedback circuit connected in parallel with the feedback capacitance configured for continuously resetting the integrator, for example continuously discharging the feedback capacitance. The feedback circuit is chosen such that the amplifier still functions as an integrator but gradually discharges the feedback capacitance. There is a feedback circuit for each of the at least one pulse shaper circuit. The feedback circuit could for example be a current source or a discharge resistance.

The at least one pulse shaper circuit further comprises a first switching unit connected in series with the feedback circuit and configured for disabling the feedback circuit when open. In some examples the first switching unit is a solid-state switching unit or switch. There is a first switching unit for each of the at least one pulse shaper circuit. The at least one pulse shaper circuit further comprises a second switching unit connected in parallel with the amplifier. For example, the second switching unit could be connected between the input and output of the amplifier or connected across the feedback capacitance if it is present. There is a second switching unit for each of the at least one pulse shaper circuit. The second switching unit may also be implemented as a solid-state switch or switching unit.

The at least one pulse shaper circuit further comprises a discriminator circuit connected to the amplifier output. The discriminator circuit is configured for providing a discriminator signal when the amplifier output exceeds a controllable signal threshold. There is a discriminator circuit for each of the at least one pulse shaper circuit. The controllable signal threshold may for example be programmable, controllable, or adjustable.

The at least one pulse shaper circuit may comprise a control unit for controlling the first switching unit and the second switching unit, wherein the control unit controls the second switching unit such that a substantial part of the signal is integrated, when the second switching unit is closed.

In another embodiment, the at least one control unit comprises a timing circuit configured for controlling the first switching unit and the second switching unit. The timing circuit may for example be implemented as a controller or it may also be implemented as analogue electronics. The timing circuit is configured for receiving the discriminator signal. The timing circuit is configured for opening the first switching unit upon receiving the discriminator signal or in response to receiving the discriminator signal. The timing circuit is further configured for closing the second switching unit after a first delay. The timing circuit is configured for opening the second switching unit after a second delay after closing the second switching unit. In some examples, the timing circuit is configured for closing the first switching unit after a third delay. In other examples the timing circuit is configured for closing the first switching unit while the second switching unit is closed or while the second switching unit is being closed.

This embodiment may be advantageous because it provides for a pulse shaper that more accurately provides an output pulse that is proportional or related to the energy of an incoming or detected ionizing radiation. When the timing circuit receives the discriminator signal the first switching unit is opened and this effectively removes the feedback circuit (i.e. e.g. the discharge resistance or the current source) from the circuit. The feedback circuit is no longer in parallel with the feedback capacitance and this removes the filter like effect of the discharge resistance.

For large pulses coming in there is less BD of the signal. The first delay may be chosen so that there is enough time to collect all or substantially all of the current from the direct conversion radiation detector. After this first delay the second switching unit is closed and the second switching unit effectively short circuits the feedback capacitance. This helps the integrator of the pulse shaper to form a narrow pulse. After the second delay the feedback capacitance has been effectively discharged or drained sufficiently. After the second delay the second switching unit is opened so that the amplifier again operates as an integrator.

In another embodiment the first delay is controllable and/or programmable.

In another embodiment the second delay is controllable and/or programmable.

In another embodiment the third delay is controllable and/or programmable.

In another embodiment, the control unit comprises a maximum detector connected to the amplifier output and configured for detecting a maximum of the output signal. The control unit is configured to close the second switching unit when the maximum is detected. The control unit is configured for opening the first switching unit in response to receiving the discriminator signal. The control unit is configured to close the first switching unit after a fourth delay. The control unit is further configured for opening the second switching unit after a fifth delay.

In another embodiment the fourth delay is controllable and/or programmable.

In another embodiment, the fourth delay is a delay between detecting the maximum of the output signal. In some embodiments the fourth delay is configured so that the first switching unit closes immediately upon detection of the maximum of the output signal. In other embodiments the delay is configured such that the first switching unit closes after the second switching unit has closed or while the second switching unit is closing.

In another embodiment the fifth delay is controllable and/or programmable. In some embodiments the fifth delay is configured such that the second switching unit closes as soon as the maximum of the output signal is detected.

In another embodiment the radiological instrument comprises a direct conversion radiation detector for each of the at least one pulse shaper circuit. This embodiment may be beneficial because the pulse shaper circuit can be adjusted to work optimally with its direct conversion radiation detector.

In another embodiment the direct conversion radiation detector is a cadmium zinc telluride detector.

In another embodiment the direct conversion radiation detector is a cadmium telluride detector.

In another embodiment the direct conversion radiation detector is an amorphous selenium detector.

In another embodiment the direct conversion radiation detector is a silicon doped with lithium detector.

In another embodiment the direct conversion radiation detector is germanium doped with lithium detector.

In another embodiment the at least one pulse shaper circuit is multiple pulse shaper circuits. In other words, instead of just one pulse shaper circuit there are multiple pulse shaper circuits. The radiological instrument comprises a radiation detector array comprising or connected to the multiple pulse shaper circuits. This for example may be useful in manufacturing various imaging systems such as CT systems, digital X-ray systems and others.

In another embodiment the radiological instrument further comprises a pulse height analyzer connected to the shaper output. This embodiment may be beneficial because the pulse height analyzer is used to count the number of pulses within a particular voltage or energy range. The use of the at least one pulse shaper circuit may provide for a more accurate count in the different channels.

A pulse height analyzer as used herein encompasses an instrument configured for counting the number of pulses falling within each of one or more predetermined or adjustable amplitude ranges. A pulse height analyzer may also be referred to as a kick-sorter or a multi-channel analyzer (MCA).

In another embodiment the first delay is between 5 ns and 30 ns. This embodiment may be beneficial because depending upon the type of direct conversion radiation detector the complete current from the detector can be collected after an ionizing radiation has caused an event in the detector.

In another embodiment the first delay is between 8 ns and 30 ns. This embodiment may be beneficial because it may provide for even better measurement of the current produced by the direct conversion radiation detector.

In another embodiment the second delay is between 1 ns and 10 ns. This embodiment may be beneficial because this amount of time may be sufficient to discharge the feedback capacitance and ready the at least one pulse shaper circuit to receive another pulse.

In another embodiment the second delay is between 3 ns and 5 ns. This embodiment may be beneficial because it provides for a more accurate time range in which to drain a realistic feedback capacitance.

In another embodiment the first delay and/or the second delay are programmable and/or controllable. This for example may be accomplished in some examples by the timing circuit being a controller or microcontroller. In other examples the timing circuit may be an analogue circuit which may be configured. Being able to program the first delay and/or the second delay may be beneficial because it may provide for output pulses which have a height which is more accurate in relation to the energy absorbed by the direct conversion radiation detector.

In another embodiment the second switching unit is configured as a short circuit. This embodiment may be beneficial because the short circuit may be used to quickly drain the discharge resistance and enable the pulse shaper circuit to be ready to receive another input signal.

In another embodiment the short circuit has a short circuit resistance. The short circuit resistance is less than the discharge resistance. This embodiment may be beneficial because it may enable the feedback capacitance to be drained more rapidly.

In another aspect, the invention provides for an imaging system comprising a radiation detector array. This embodiment may be beneficial because the use of the first switching unit and the timing circuit may provide for an imaging system that uses less ionizing radiation to image a subject. This may for example reduce the health risks associated with performing a scan with the imaging system. This embodiment may also be further beneficial because the pulse shaper circuit may enable more accurate energy discrimination or spectroscopy of ionizing radiation. This may for example provide for improved quality of images that are generated or acquired by the imaging system.

In another embodiment the imaging system further comprises a memory and a processor. The memory contains machine-executable instructions and imaging system control commands. Execution of the machine-executable instructions further causes the processor to receive configuration commands. The configuration commands comprise control unit configuration data. In some embodiments the control unit configuration data comprises time delay configuration data. The configuration commands may also comprise data for configuring the controllable signal threshold.

Execution of the machine executable instructions causes the processor to receive configuration commands—The configuration commands comprise control unit configuration data. Execution of the machine executable instructions further causes the processor to configure the control unit with the control unit configuration data. Execution of the machine executable instructions further causes the processor to acquire imaging data by controlling the imaging system with the imaging system control commands.

In another embodiment the control unit is implemented using a timing circuit. The control unit configuration data comprises time delay configuration data. Execution of the machine-executable instructions causes the processor to control the timing circuit to configure the first delay and/or the second delay with the time delay configuration data. The third delay may also be configured by the time delay configuration data.

In this step the controllable signal threshold may also be configured. Execution of the machine-executable instructions further causes the processor to acquire imaging data (such as medical imaging data) by controlling the imaging system with the imaging system control commands. The imaging system control commands are instructions or data which may be converted into instructions which are used for controlling the operation and function of the imaging system. This embodiment may be beneficial because it may provide a means for tailoring the configuration of the at least one pulse shaper circuit for a particular imaging protocol. This for example may result in reduced exposure to radiation by the subject and it may also provide for improved spectroscopic resolution in the imaging data.

In another embodiment the imaging system is a computed tomography system.

In another embodiment the imaging system is a positron emission tomography (PET) scanner.

In another embodiment the imaging system is a single photon emission computed tomography (SPECT) system or scanner.

In another embodiment the imaging system is a digital X-ray system. For example, the digital X-ray system may be a digital fluoroscope system.

In another embodiment the imaging system is a computed tomography system. The computed tomography system comprises a rotatable gantry. The rotatable gantry comprises an X-ray source and the radiation detector array. The radiation detector array may be arranged such that it is able to measure absorption profiles from the X-ray source as the gantry rotates about a subject. The computed tomography system is a spectral computed tomography system. This embodiment may be beneficial because the use of the at least one pulse shaper circuit may provide for improved spectral resolution for a spectral computed tomography system.

In another aspect the invention provides for a computer program product comprising machine-executable instructions for execution by a processor controlling an imaging system. The imaging system comprises pulse shaper circuits. The pulse shaper circuits are each configured for receiving an input signal from a separate direct conversion radiation detector. The pulse shaper circuits each comprise a shaper input configured for receiving the input signal. The pulse shaper circuits each comprise a shaper output configured for providing an output signal in response to the input signal. The pulse shaper circuits each comprise an amplifier with an amplifier input connected to the shaper input and an amplifier output connected to the shaper output. The amplifier is configured as an integrator.

The pulse shaper circuits may each comprise a feedback capacitance connected between the amplifier input and the amplifier output. The pulse shaper circuits each comprise a feedback circuit, such as a discharge resistance or current source, connected in parallel with the amplifier, or if present the feedback capacitance, configured for continuously resetting the integrator. For example, by discharging feedback capacitance if present. The pulse shaper circuits each comprise a first switching unit connected in series with the feedback circuit and configured for disabling the feedback circuit when open.

The pulse shaper circuits each comprise a second switching unit connected in parallel with the amplifier or the feedback capacitance configured for either resetting the integrator or for discharging the feedback capacitance when closed. The pulse shaper circuits each comprise a discriminator circuit connected to the amplifier output. The discriminator circuit is configured for providing a discriminator signal when the amplifier output exceeds a controllable signal threshold. The pulse shaper circuits each comprise a control unit configured for controlling the first switching unit and the second switching unit.

The imaging system further comprises a direct conversion radiation detector for each of the pulse shaper circuits. The imaging system further comprises a radiation detector array comprising or connected to the multiple pulse shaper circuits. The imaging system further comprises an imaging system. The imaging system further comprises a memory and a processor. The memory contains machine-executable instructions and imaging system control commands. Execution of the machine-executable instructions causes the processor to receive configuration commands. The configuration commands comprise control unit configuration data.

Execution of the machine-executable instructions further causes the processor to control the timing circuit to configure the control unit with the control unit configuration data. Execution of the machine-executable instructions further causes the processor to acquire imaging data by controlling the imaging system with the imaging system control commands. In some embodiments the imaging data may be reconstructed by the processor into an image.

In another aspect the invention provides for a method of operating an imaging system. The imaging system comprises pulse shaper circuits. The pulse shaper circuits are each configured for receiving an input signal from a separate direct conversion radiation detector.

The pulse shaper circuits each comprise a shaper input configured for receiving the input signal. The pulse shaper circuits each comprise a shaper output configured for providing an output signal in response to the input signal. The pulse shaper circuits each comprise an amplifier with an amplifier input connected to the shaper input and an amplifier output connected to the shaper output. The amplifier is configured as an integrator. The pulse shaper circuits may each comprise a feedback capacitance connected between the amplifier input and the amplifier output. The pulse shaper circuits each comprise a feedback circuit, such as a discharge resistance or a current source, connected in parallel with the feedback capacitance configured for continuously discharging the feedback capacitance. The pulse shaper circuits each comprise a first switching unit connected in series with the feedback circuit and configured for disabling the feedback circuit when open. The pulse shaper circuits each comprise a second switching unit connected to the amplifier input and output or in parallel with the feedback capacitance.

The pulse shaper circuits each comprise a discriminator circuit connected to the amplifier output. The discriminator circuit is configured for providing a discriminator signal when the amplifier output exceeds a controllable signal threshold. The pulse shaper circuits each comprise a control unit configured for controlling the first switching unit and the second switching unit. The control unit is configured for receiving the discriminator signal. The timing circuit is configured for opening the first switching unit such that a substantial part of the signal is integrated.

The imaging system further comprises a direct conversion radiation detector for each of the one pulse shaper circuits. The imaging system comprises a radiation detector comprising or connected to the multiple pulse shaper circuits and the direct conversion radiation detector for each of the one pulse shaper circuits. The imaging system further comprises an imaging system. The imaging system further comprises a memory and a processor. The memory contains machine-executable instructions and imaging system control commands.

The method comprises receiving configuration commands. The configuration commands comprise control unit configuration data. The method further comprises configuring the control unit with the control unit configuration data. The method further comprises acquiring imaging data by controlling the imaging system with the imaging system control commands.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system". Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Imaging data is defined herein as being the recorded measurements of data acquired by an imaging system. The imaging data may also be referred to in some cases as medical imaging data or in other cases as tomographic imaging data. The imaging data may be reconstructed into one or more images to visualize structures of a subject. This visualization can be performed using a computer.

In some examples such as CT a tomographic reconstruction can be performed. For CT systems, the imaging data may be X-ray absorption profiles that can be used to reconstruct a tomographic image.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
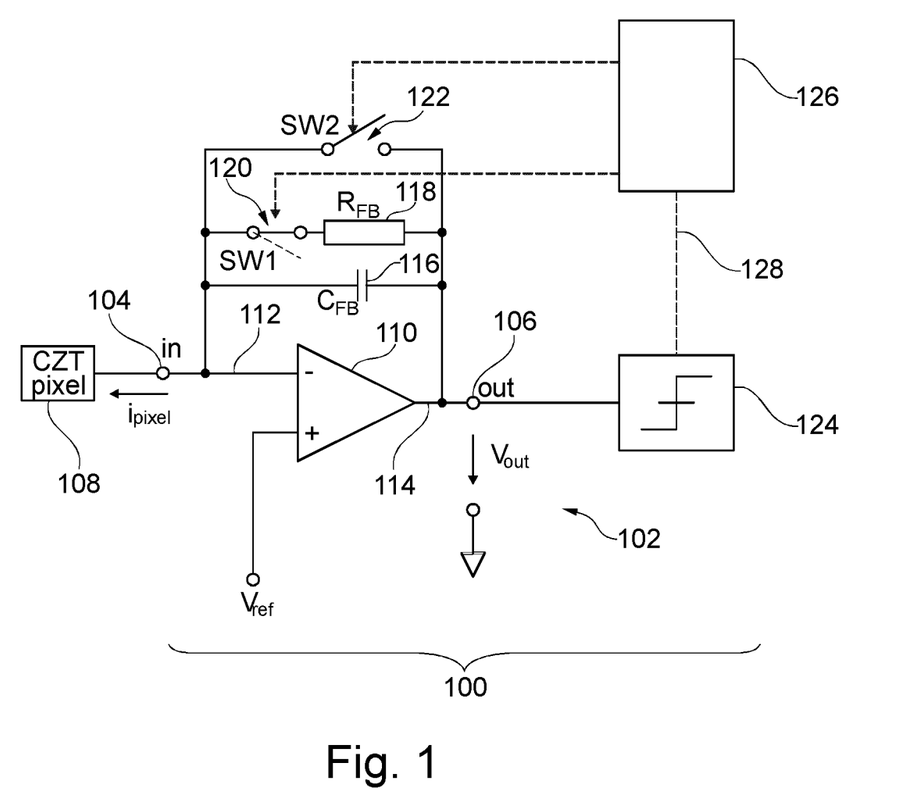
FIG. 1 illustrates an example of a radiological instrument.

FIG. 1 illustrates an example of a radiological instrument 100. The radiological instrument 100 comprises a pulse shaper circuit 102. The pulse shaper circuit 102 has a shaper input 104 for receiving a signal and a shaper output 106 for outputting a shaped signal. The radiological instrument 100 is shown as being connected to a direct conversion radiation detector 108. In some examples the direct conversion radiation detector 108 will be part of the radiological instrument 100 and in other examples it will not. For example, multiple pulse shaper circuits could be used to make a pixelated radiation detector with multiple direct conversion radiation detectors 108. In other examples the pulse shaper circuit 102 may be provided in a separate circuit which may be used to construct various experiments. For example, the pulse shaper circuit 102 could be provided in the form of a nuclear instrumentation module (NIM).

The pulse shaper circuit 102 is shown as comprising an amplifier 110 with an amplifier input 112 and an amplifier output 114. The amplifier 110 is configured as an integrator. There is therefore a feedback capacitance 116 between the amplifier input 112 and the amplifier output 114. There is also a discharge resistance 118 which functions as a feedback resistance but in this use also serves to gradually discharge the feedback capacitance 116. There is a first switching unit 120 that is in series with the discharge resistance 118. The discharge resistance in this and other circuits may be replaced with a current source. The current of this current source is then controlled by the voltage between the input and the output of the amplifier, and the provided current may depend on this voltage. There is a second switching unit 122 that is in parallel with the feedback capacitance 116. The second switching unit 122 functions as a short circuit for discharging the feedback capacitance 116. In some cases, the second switching unit 122 may also be in series with a short circuit resistance. In this case the short circuit resistance will be much less than the discharge resistance 118.

The amplifier output 114 is connected to a discriminator circuit 124. When the voltage output of the amplifier output 114 rises above a controllable signal threshold then the discriminator circuit 124 provides a discriminator signal 128. This causes the first switching unit 120 to open immediately and a timing circuit 126 then causes the second switching unit 122 to close after a first delay. The timing circuit 126 can then be configured to reopen the second switching unit 122 after a second delay from when it was initially closed. The timing circuit 126 can also be configured to close the first switching unit 120 when the second switching unit 122 is still closed.

The opening of the first switching unit 120 has the effect of removing the discharge resistance 118 temporarily from the circuit. This helps to reduce the ballistic deficit effect. When the voltage signal at the output 114 is rising quickly the output signal can be distorted which may cause a change in the height of the voltage pulse that is output. Removing the discharge resistance 118 from the circuit helps to reduce the ballistic deficit, since from the point in time of opening the first switching unit incoming charge is no longer drained via the discharge resistance. The timing circuit 126 can be programmed for the first delay to wait until all of the current or a significant portion of the current from the direct conversion radiation detector 108 has been collected. The closing of the second switching unit 122 then rapidly discharges the feedback capacitance 116. This helps to prepare the pulse shaper circuit 102 to quickly be in a state to receive another pulse from the direct conversion radiation detector 108.

Figure 2:
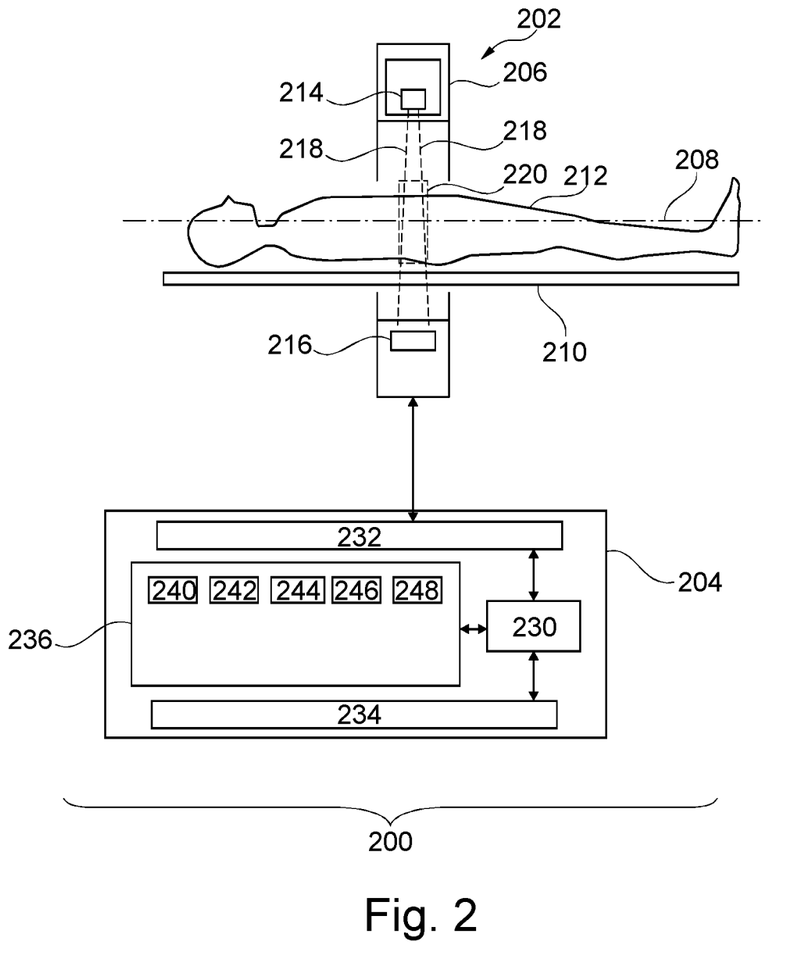
FIG. 2 illustrates a further example of an imaging system.

FIG. 2 shows an imaging system 200. In this example the imaging system 200 is shown as comprising a CT system 202 and a computer 204. The CT or computed tomography system 202 has a rotating gantry 206 that has an axis of rotation or symmetry 208. There is a subject support 210 which supports a subject 212 within the rotating gantry 206. Within the rotating gantry 206 is an X-ray tube 214 which is opposite a radiation detector array 216. The radiation detector array 216 is constructed from pixelated arrays of direct conversion radiation detectors 108 connected to pulse shaper circuits 102 such as is illustrated in FIG. 1.

In some examples the radiation detector array 216 may also contain pulse height analyzers for outputting the large amounts of data to the computer 204. The X-ray tube 214 is shown as producing X-rays 218 which pass through the subject within an imaging zone 220. The X-rays are then received by the radiation detector array 216. The use of the pulse shaping circuits 102 may enable a reduction in the amount of radiation needed to produce a computed tomography image. The computed tomography system 200 may also be a multi-spectral computed tomography system. In this case the high voltage of the X-ray tube 214 may be varied. Typically, the high voltage oscillates between two voltages. The X-ray spectra taken of these two voltages is then compared to make a multi-spectral computed tomography image. The use of the pulse shaping circuits 102 may increase the accuracy of multi-spectral computed tomography images.

The computed tomography system 202 is shown as being connected to a hardware interface 232 of the computer system 204. The hardware interface 232 is connected to a processor 230. The processor 230 is also shown as being connected to an optional user interface 234 and a memory 236. The hardware interface 232 may enable the processor 230 to send and receive commands and data from the computed tomography system 202. The hardware interface 232 may also be used to network the computer 204 with other computer systems.

The memory 236 is shown as containing machine-executable instructions 240. The machine-executable instructions 240 contain commands which enable the processor 230 to control the operation and function of the imaging system 200 as well as to perform various data analysis and image processing tasks.

The memory 236 is further shown as containing imaging system control commands 242. These are commands or data which may be converted into commands which control the sequential operation of the computed tomography ring 202 to acquire imaging data. The memory 236 is further shown as containing configuration commands 244 that comprise time delay configuration data. The time configuration data may be used to program the first delay and/or the second delay.

The memory 236 is shown as containing imaging data 246 that has been acquired by controlling the computed tomography system 202 with the imaging system control commands 242 and programming the timing circuit 126 with the time configuration data. Finally, the memory 236 is shown as having an image 248 which has been reconstructed from the imaging data 246. In this example the imaging data 246 will be X-ray absorption profiles and the image 248 will be a computed tomography image.

Figure 3:
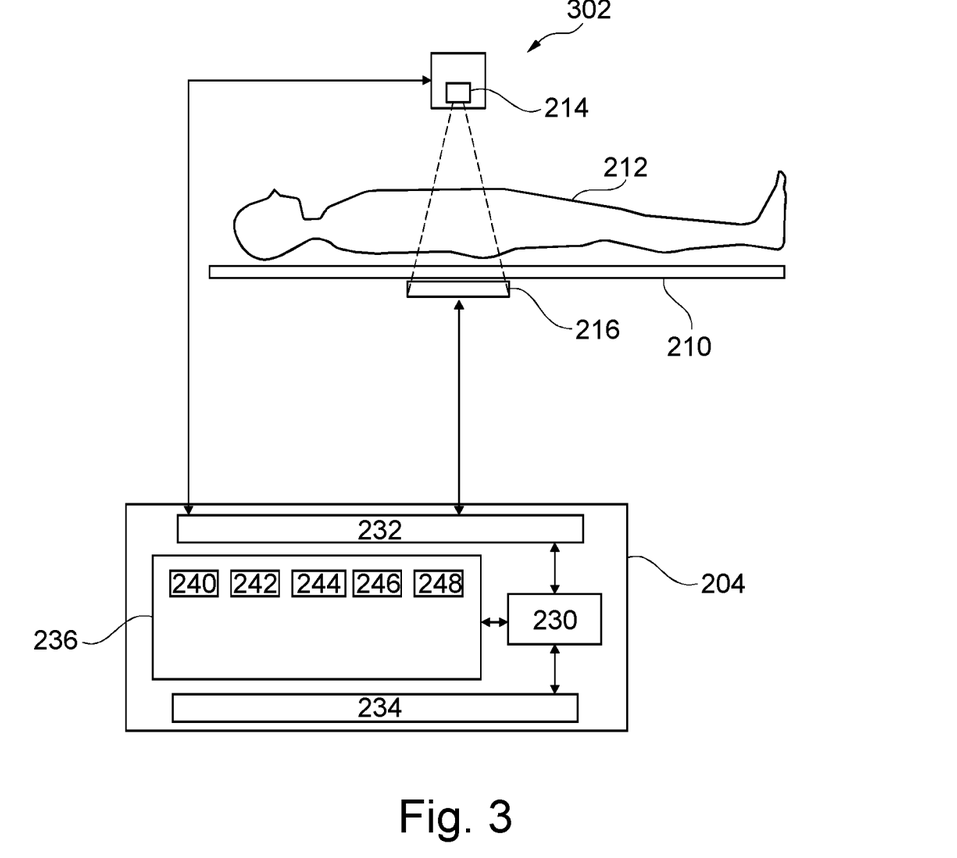
FIG. 3 illustrates a further example of an imaging system.

FIG. 3 illustrates a further example of an imaging system 300. The imaging system 300 illustrated in FIG. 3 is similar to the imaging system 200 in FIG. 2 except the computed tomography system 202 has been replaced with an X-ray system 302. The X-ray system comprises an X-ray tube 214 which transmits X-rays 218 through the subject 212 to a radiation detector array 216. The X-ray system 302 is therefore a digital X-ray system. For example, the X-ray system 302 could be a digital fluoroscope system. The X-ray tube 214 and the radiation detector array 216 are shown as being controlled by the hardware interface 232 of the computer system 204.

Figure 4:
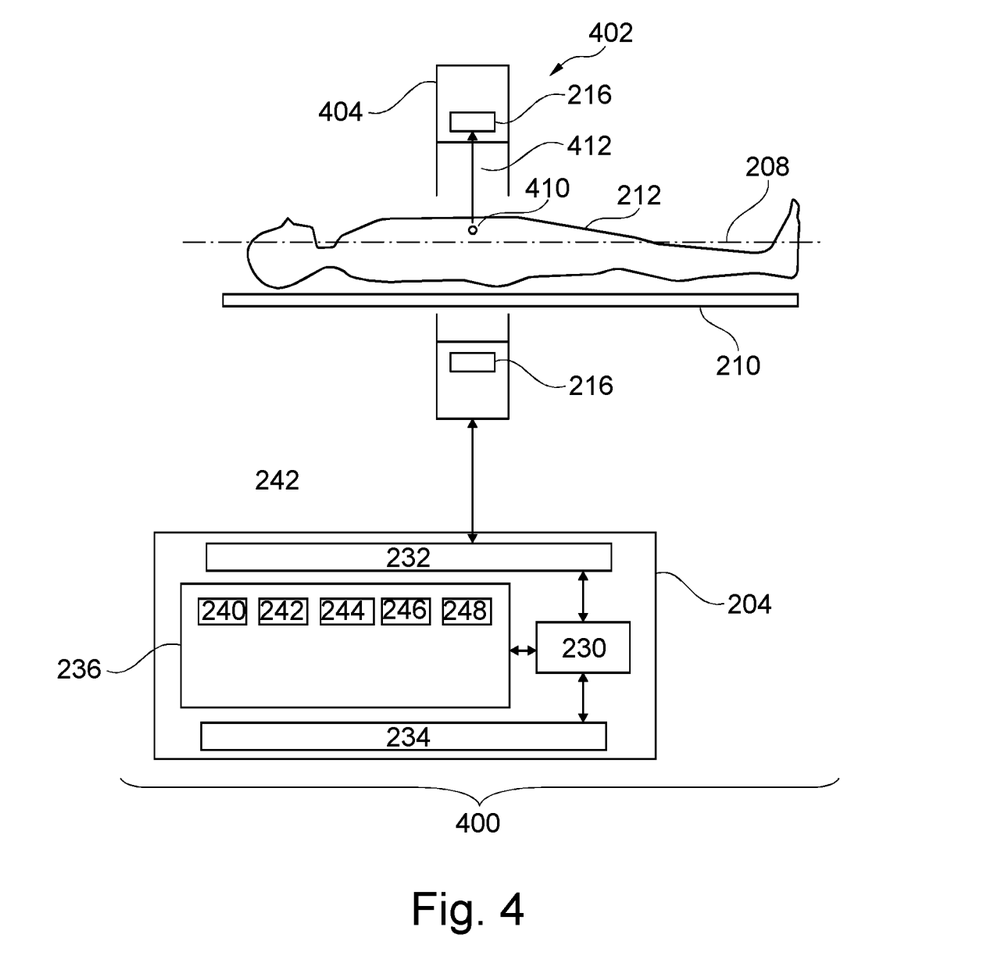
FIG. 4 illustrates a further example of an imaging system.

FIG. 4 illustrates a further example of an imaging system 400. The imaging system 400 of FIG. 4 is similar to the imaging systems illustrated in FIGS. 2 and 3 except the imaging system in this case is a single photon emission computed tomography system 402. The single photon emission computed tomography system 402 comprises a detector ring 404 with an axis of symmetry 208. The detector ring 404 comprises multiple detector rays 216 arranged in the ring. The subject 212 has ingested a radionuclide 410. The radionuclide undergoes decay and emits a single gamma photon 412. The system acquires multiple gamma radiation events 412 using the detector arrays 216. When enough data has been collected in the imaging data 246 an image 248 is reconstructed. Although it is not depicted, a similar arrangement could be used to construct a positron emission tomography system.

Figure 5:
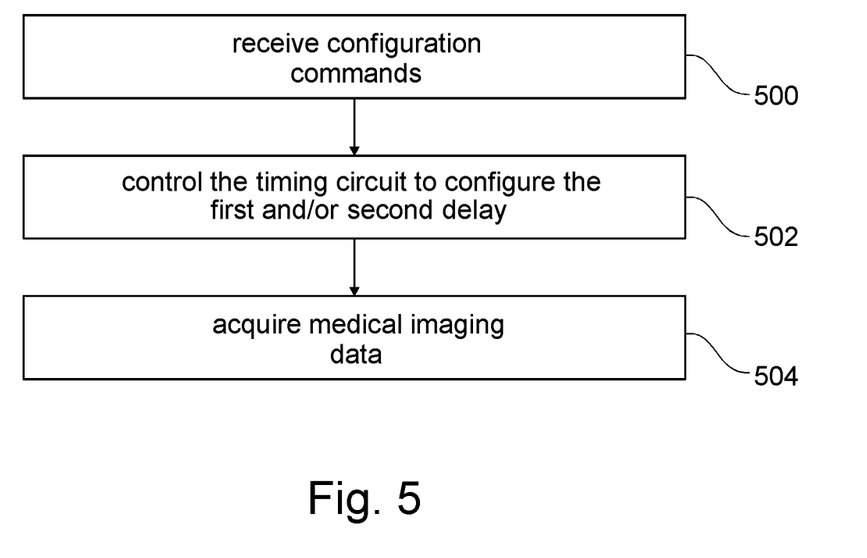
FIG. 5 shows a flowchart which illustrates an example of a method of operating the imaging system of claim 2, 3, or 4.

FIG. 5 shows a flowchart which illustrates a method of operating any of the imaging systems 200, 300, 400 shown in FIG. 2, 3 or 4. First in step 500 the configuration commands 244 are received. In some instances, the configuration commands 244 may be part of the imaging system control commands 242. For example, for a particular imaging protocol the configuration of the first and second delay could be programmed into the imaging system control commands 242. Next in step 502 the timing circuit 126 is controlled with the configuration commands 242. The configuration commands 242 control time delay configuration data which is used to set or configure the first delay and/or the second delay. In step 502 the time delay configuration data is used to configure the first delay and the second delay. Finally, in step 504, the imaging system 202, 302, 402 is controlled with the imaging system control commands 242 to acquire the imaging data 246. In some further examples the imaging data 246 is reconstructed into an image 248.

Examples may provide for shaping circuits support high count rate at a good enough SNR with sufficient homogeneity across pixel channels. To simultaneously address the SNR issues and adequately address the count-rate requirements it is required to ensure that the complete charge collection has taken place before allowing the feedback capacitance to discharge. In this way, no ballistic deficit may occur.

Due to the high X-ray flux in human CT, in so-called "paralyzable" analog front-ends (AFE), which exhibit besides an integrating capacitance e.g. a resistive feedback that results in pulse shaping (so-called "continuous reset", see below), the observed count-rate (OCR) as a function of the incident count-rate (ICR) drops after a maximum (OCR-max) has been reached so that there is no monotonic relationship between OCR and ICR. This is caused by the relatively long deadtime of about 30 ns that can be achieved with such AFEs at reasonable power requirements in conjunction with the choice of the pixel-size (e.g. 500 µm), which should not be too small in order to avoid that charge sharing destroys the energy-resolution.

In order to support higher count rates by reducing the deadtime, thus increasing the ICR range, in which the OCR monotonically increases with the ICR, the concept of discharging the feedback capacitance Cfb (116) by closing a switch (second switching unit 122) after each event (often called "Cfb reset") may be used. Here discharging is triggered by the integrator's output voltage exceeding a lowest energy threshold LT (controllable signal threshold). As a result of the reset, the resulting SHA output pulse gets significantly shorter than 30 ns, ideally not larger than the largest charge collection time of X-ray events in the crystal (e.g. 13 ns). This Cfb reset has to be combined with a feedback resistance Rfb (discharge resistance 118) to eliminate events, the energy of which is below the lowest energy threshold (below-LT events). Without Rfb, Cfb just integrates the charge of below-LT events so that the energy estimation of above-LT events becomes wrong. Since Rfb implements a continuous reset of Cfb, Cfb is discharged autonomously by Rfb so that the output voltage of the charge integrator always returns to the baseline for below-LT events.

This approach has the drawback that Rfb, even if a large value is used, contributes to the ballistic deficit so that the charge integrator's output voltage dependency on the CZT (or other direct conversion detector) pulse duration is not fully eliminated. Rfb cannot be chosen very large, since otherwise below-LT events will cause very long small pulses resulting in a long tail, which falsifies the energy estimation of above-LT events, which pile-up on this tail. To eliminate this problem a first switching unit is placed in series with the Rfb that disconnects the Rfb while an above-LT event is being processed, is described.

Hence, it is proposed to combine both ideas to get to a low ballistic-deficit SHA in which the OCR monotonically follows the ICR (so-called "non-paralyzable" count rate behavior).

A pulse shaper (SHA) may have one or more of the following features:

a) integrates the generated current pulse,
b) detects that the incoming pulse has an energy larger than the lowest energy threshold set
c) disconnects the feedback resistance Rfb until the feedback capacitance Cfb is discharged
d) waits for the maximum possible charge collection time as given by the direct conversion material and then discharges the feedback capacitance Cfb to make the SHA ready for the next CZT pulse. In the time-vicinity of the reset operation Rfb is reconnected again.

Alternatively, d) may be replaced by detecting that the output voltage of the SHA has reached a maximum, i.e. does not change anymore, which indicates that charge collection for this event has finished, and discharge Cfb when the maximum has been reached.

Due to the Cfb reset, the deadtime of this AFE is determined by the maximum charge collection time (usually in the range of 13 ns) so that the maximum possible OCR (observed count rate) can be pushed to larger values than e.g. 15 Mcps/pix.

Figure 6:
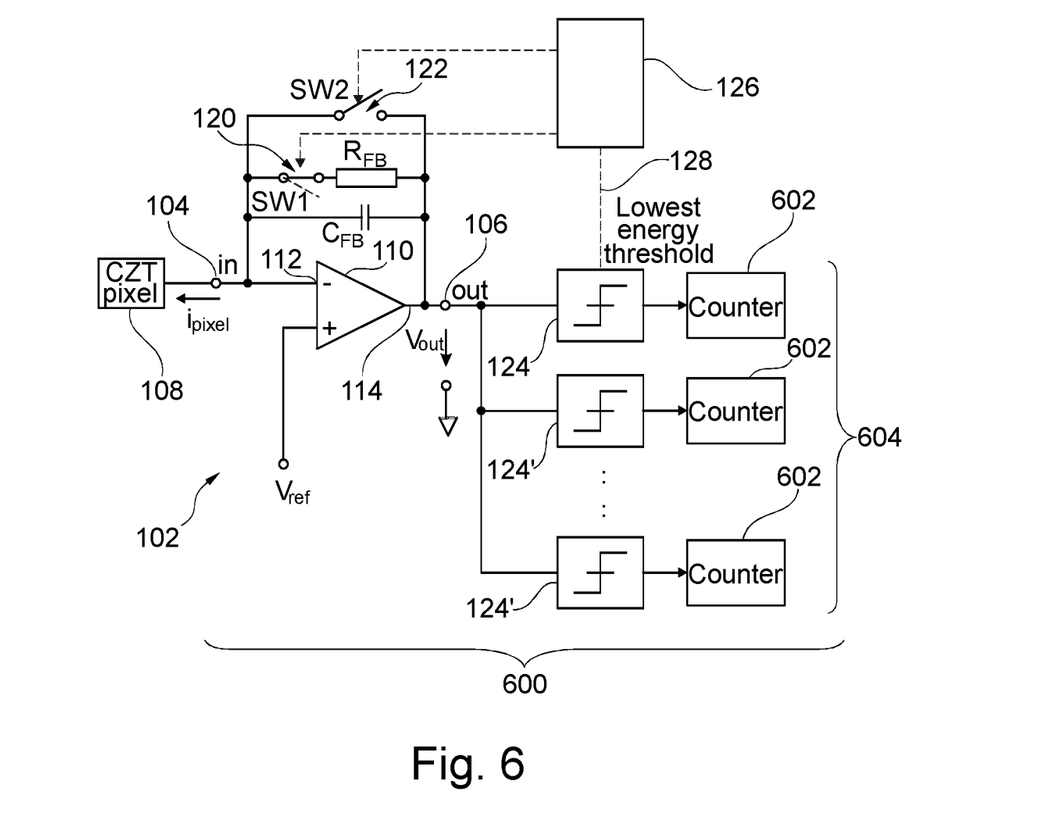
FIG. 6 illustrates a further example of a radiological instrument.

FIG. 6 shows a further example of a radiological instrument 600. The radiological instrument 600 in FIG. 6 is similar to the circuit illustrated in FIG. 1. The radiological instrument is additionally shown as comprising a pulse height analyzer 604. There are additional discriminator circuits 124'. All of the discriminator circuits 124' including the discriminator circuit used to generate the discriminator signal 128 are connected to counters 602. The discriminator circuit 124 has the lowest energy threshold within the pulse height analyzer 604.

FIG. 6 shows a possible implementation. The lowest energy threshold (controllable signal threshold) is used to determine whether an above-LT pulse is being generated, which has to be counted without ballistic deficit. Hence, when LT is exceeded, Rfb is disconnected from Cfb so that from then on, Cfb can be charged without any loss in charge, which would otherwise cause (additional) ballistic deficit and therefore result in small amplitude changes of Vout resulting from variations in the charge collection time of events of the same energy. When Vout has exceeded LT, also a timer is started (e.g. a digital counter for time increments or an analog implementation). This timer is dimensioned such that the largest possible (remaining) charge collection time is waited for, until Cfb is discharged by closing SW2.

Alternatively, a dedicated lowest threshold in addition to the normal energy thresholds used for spectral acquisition, can be stipulated (cf. FIG. 7 below), in which case this threshold need not be connected to a counter, since its only purpose is to detect "real" pulses, i.e. those, which are to be analyzed for energy by the set of discriminators connected to counters.

Figure 7:
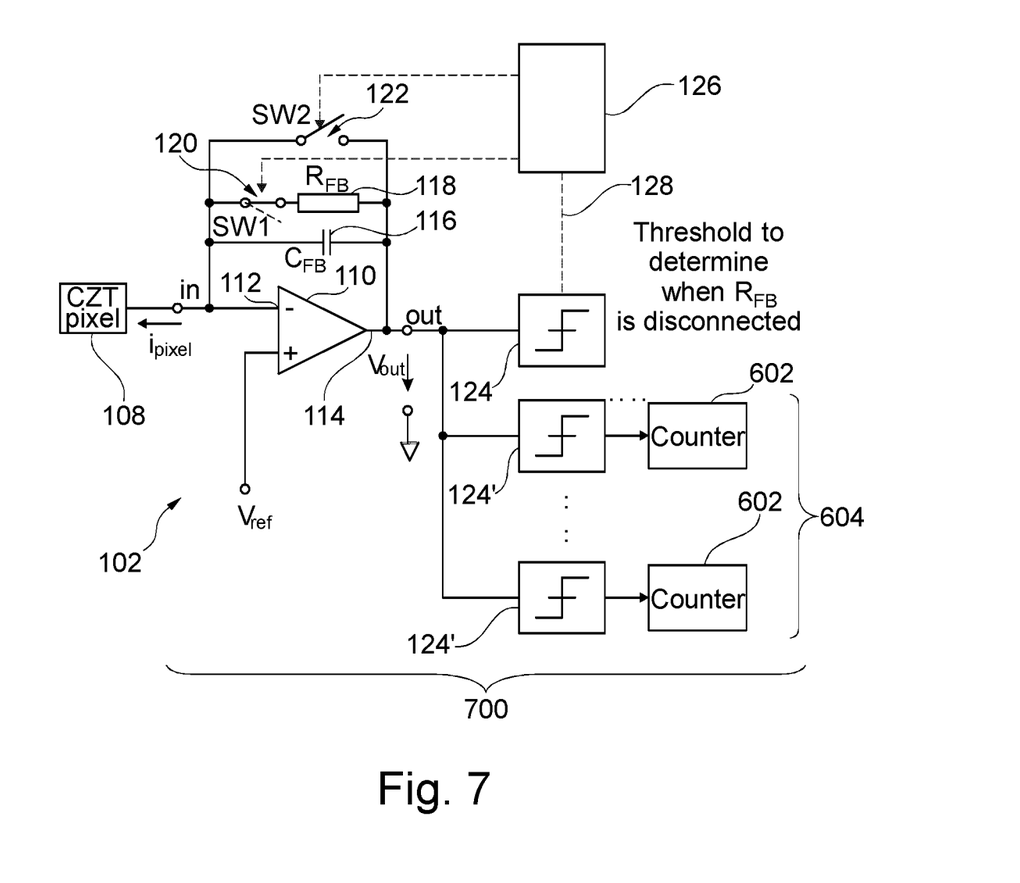
FIG. 7 illustrates a further example of a radiological instrument.

FIG. 7 shows a further example of a radiological instrument 700. The circuit illustrated in FIG. 7 is similar to that of FIG. 6 except in this case the discriminator circuit 124 used to generate the discriminator signal 128 is not part of the pulse height analyzer 604. This has the advantage of being able to set the threshold to a lower value than is analyzed by the pulse height analyzer 604. In FIG. 7 the threshold to detect, whether the feedback resistance is to be disconnected, is not used for an energy measurement, and therefore does not have a counter. In another example, the reset may be done using the charge-pump approach in order to minimize charge loss, which can occur, if during short-circuiting Cfb another event arrives. In the implementation of FIG. 6 and FIG. 7, such an event would be lost partially or fully.

Dealing with dark and persistent currents. Usually, the sensor will exhibit a dark current. When Rfb is disconnected, there is no resistive path for this current anymore, i.e. the dark current will charge Cfb and thus cause a wrong energy reading for the event, which is being processed. E.g. for a duration of e.g. 20 ns, in which Rfb is being disconnected, a dark current of 100 pA will cause a change in collected charge of 100 pA×20 ns=0.002 fC, which has to be assessed in comparison with the charge of the lowest energy photon, e.g. a 20 keV photon that is to be collected, which charge is 0.690 fC, i.e. the measured energy of the 20 keV photon is 0.03% too large. This appears reasonably low, especially if the dark current does not change; such a deterministic offset can also be eliminated by calibration. For larger dark currents, circuitry for static leakage current compensation are available: Before a measurement, the dark current is measured in each pixel and during the measurement, this measured value is subtracted from the current that is received from the sensor pixel. For larger persistent currents, i.e. additional background currents that come into being due to charge injection, while X-ray photons are interacting with the sensor crystal, a baseline restorer would be needed.

For a continuous reset implemented by means of injection of a current could be used, redirecting this feedback current away from the input node so that discharging is stopped, if LT is exceeded, seems in principle possible, is however less straight-forward than disconnecting Rfb.

Figure 8:
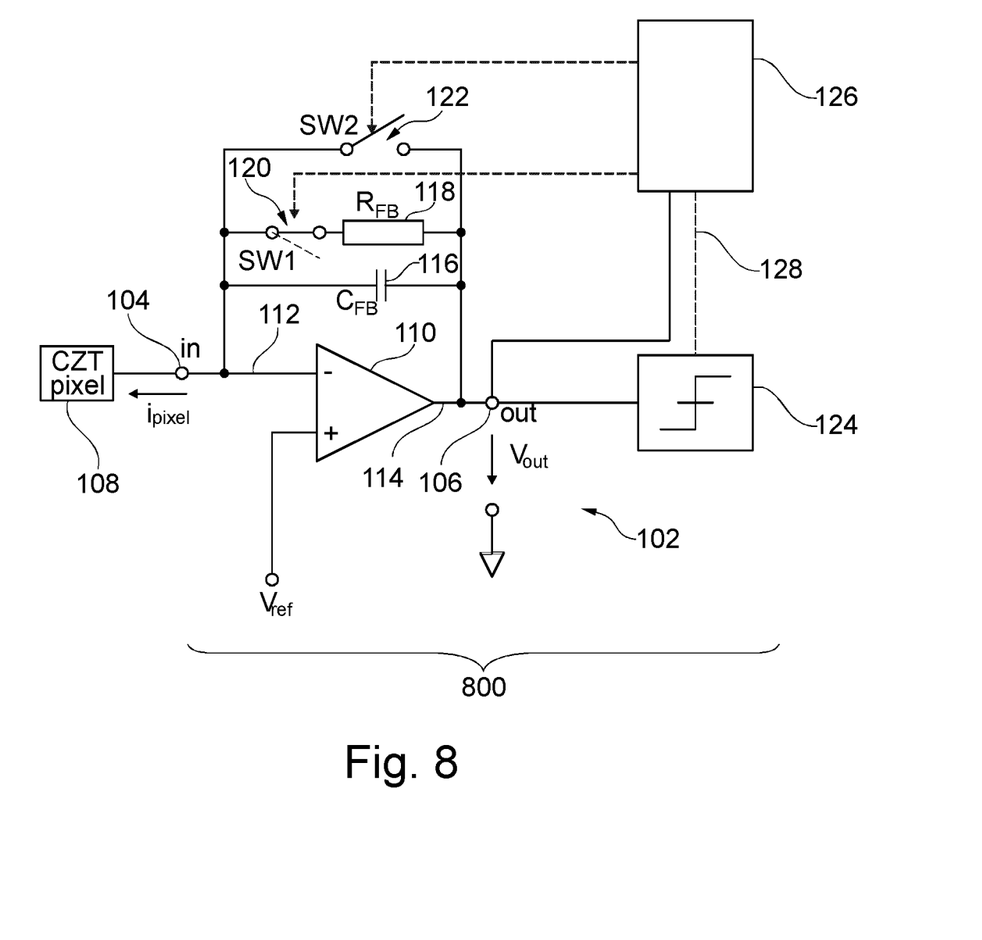
FIG. 8 illustrates a further example of a radiological instrument.

FIG. 8 shows a further example of a radiological instrument 800. The radiological instrument 800 is similar to the radiological instrument 100 depicted in FIG. 1. Except that the controller 126 is shown as also having a direct connection to the output 106. The controller may additionally comprise a maximum detector that is configured for detecting a maximum of the output signal. The control unit could for example be configured for opening the first switching unit in response to receiving the discriminator signal. The control unit could further be configured to close the first switching unit after a fourth delay. The control unit could further be configured for opening the second switching unit after a fifth delay.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 radiological instrument
102 pulse shaper circuit
104 shaper input
106 shaper output
108 direct conversion radiation detector
110 amplifier
112 amplifier input
114 amplifier output
116 feedback capacitance
118 discharge resistance
120 first switching unit
122 second switching unit
124 discriminator circuit
124' discriminator circuit
126 timing circuit
128 discriminator signal
200 imaging system
202 CT system
204 computer
206 rotatable gantry
208 axis of rotation or symmetry
210 subject support
212 subject
214 x-ray tube
216 radiation detector array
218 x-rays
220 imaging zone
230 processor
232 hardware interface
234 user interface
236 memory
240 machine executable instructions
242 imaging system control commands
244 configuration commands
246 imaging data
248 image
300 imaging system
302 x-ray system
400 imaging system
402 SPECT system
404 detector ring
410 radionucleide
412 gamma radiation
500 receive configuration commands
502 control the timing circuit to configure the first delay and/or the second delay with the time delay configuration data
504 acquire imaging data by controlling the imaging system with the imaging system control commands
600 radiological instrument
602 counter
604 pulse height analyzer
700 radiological instrument
800 radiological instrument

The invention claimed is:

1. A radiological instrument, comprising:
at least one pulse shaper circuit, wherein the at least one pulse shaper circuit is configured for receiving an input signal from a direct conversion radiation detector, wherein the at least one pulse shaper circuit comprises:
a shaper input configured for receiving the input signal;
a shaper output configured for providing an output signal in response to the input signal;
an amplifier with an amplifier input connected to the shaper input and an amplifier output connected to the shaper output, wherein the amplifier is configured as an integrator;
a feedback circuit connected in parallel with the amplifier and configured for continuously resetting the integrator;
a first switch connected in series with the feedback circuit and configured for disabling the feedback circuit when open;
a second switch connected in parallel with the amplifier and configured for resetting the integrator when closed;
a discriminator circuit connected to the amplifier output, wherein the discriminator circuit is configured for providing a discriminator signal when the amplifier output exceeds a controllable signal threshold; and
a controller configured to control the first switch and the second switch, wherein the controller controls the second switch such that a substantial part of the signal is integrated, when the second switch is closed; wherein the controller is a timing circuit configured for controlling the first switch and the second switch, wherein the timing circuit is configured for receiving the discriminator signal, wherein the timing circuit is configured for opening the first switch upon receiving the discriminator signal, wherein the timing circuit is configured for closing the second switch after a first delay, wherein the timing circuit is configured for opening the second switch after a second delay after closing the second switch, wherein the timing circuit is configured for closing the first switch after a third delay.

2. The radiological instrument of claim 1, wherein the radiological instrument comprises a direct conversion radiation detector for each of the at least one pulse shaper circuit.

3. The radiological instrument of claim 2, wherein the direct conversion radiation detector is any one of the following: a cadmium zinc telluride detector, a cadmium telluride detector, an amorphous selenium detector, a silicon doped with lithium detector, and germanium doped with lithium detector.

4. The radiological instrument of claim 1, wherein the at least one pulse shaper circuit further comprises a feedback capacitance connected between the amplifier input and the amplifier output, wherein the feedback circuit is configured for continuously resetting the integrator by continuously discharging the feedback capacitance, and wherein the second switch is configured for resetting the integrator by short circuiting the feedback capacitance.

5. The radiological instrument of claim 1, wherein the second switch is configured as a short circuit.

6. The radiological instrument of claim 1, wherein the feedback circuit is a current source.

7. The radiological instrument of claim 1, wherein the feedback circuit is a discharge resistance, wherein the second switch is in series with a short circuit resistance, wherein the short circuit resistance is less than the discharge resistance.

8. The radiological instrument of claim 1, wherein the radiological instrument comprises at least one radiation detector array comprising or connected to multiple of the at least one pulse shaper circuits.

9. A method of operating an imaging system, comprising:
providing pulse shaper circuits;
receiving, by the pulse shaper circuits, an input signal from a separate direct conversion radiation detector;
providing an output signal in response to the input signal;
connecting an amplifier to the shaper, wherein the amplifier is configured as an integrator;
connecting a feedback circuit in parallel with the amplifier, the feedback circuit being configured for continuously resetting the integrator;
connecting a first switch in series with the feedback circuit, the first switch being configured for disabling the feedback circuit when open;
connecting a second switch in parallel with the amplifier, the second switch being configured for resetting the integrator when closed;
connecting a discriminator circuit to the amplifier output, wherein the discriminator circuit is configured to provide a discriminator signal when an amplifier output exceeds a controllable signal threshold;
controlling the first switch and the second switch, wherein the second switch is controlled such that a substantial part of the signal is integrated when the second switch is closed;
receiving the discriminator signal;
opening the first switch upon receiving the discriminator signal;
closing the second switch after a first delay;
opening the second switch after a second delay after closing the second switch;
closing the first switch after a third delay.

10. A non-transitory computer-readable medium for storing executable instructions, which cause a method to be performed to operate an imaging system, the method comprising:
providing pulse shaper circuits;
receiving, by the pulse shaper circuits, an input signal from a separate direct conversion radiation detector;
providing an output signal in response to the input signal;
connecting an amplifier to the shaper, wherein the amplifier is configured as an integrator;
connecting a feedback circuit in parallel with the amplifier, the feedback circuit being configured for continuously resetting the integrator;
connecting a first switch in series with the feedback circuit, the first switch being configured for disabling the feedback circuit when open;
connecting a second switch in parallel with the amplifier, the second switch being configured for resetting the integrator when closed;
connecting a discriminator circuit to the amplifier output, wherein the discriminator circuit is configured to provide a discriminator signal when an amplifier output exceeds a controllable signal threshold;
controlling the first switch and the second switch, wherein the second switch is controlled such that a substantial part of the signal is integrated when the second switch is closed;
receiving the discriminator signal;
opening the first switch upon receiving the discriminator signal;
closing the second switch after a first delay;
opening the second switch after a second delay after closing the second switch;
closing the first switch after a third delay.

* * * * *